United States Patent [19]

Wallace

[11] Patent Number: 4,481,470
[45] Date of Patent: Nov. 6, 1984

[54] METHOD FOR DETERMINING THE HARDNESS OF STRAIN HARDENING ARTICLES OF TUNGSTEN-NICKEL-IRON ALLOY

[75] Inventor: Steven A. Wallace, Knoxville, Tenn.

[73] Assignee: The United States of America as represented by the United States Department of Energy, Washington, D.C.

[21] Appl. No.: 287,966

[22] Filed: Jul. 29, 1981

[51] Int. Cl.³ .................... G01R 33/12; G01N 27/72
[52] U.S. Cl. ................................... 324/228; 324/209
[58] Field of Search ............... 324/228, 229, 232, 234, 324/235, 238, 209, 200

[56] References Cited

U.S. PATENT DOCUMENTS

| | | | |
|---|---|---|---|
| 3,739,261 | 6/1973 | Renkin, Jr. | 324/232 |
| 3,980,947 | 9/1976 | Bielsten et al. | 324/209 X |
| 4,126,491 | 11/1978 | Karlsson | 324/238 |
| 4,207,519 | 6/1980 | Zatsepin et al. | 324/238 |
| 4,279,163 | 7/1981 | Takekoshi et al. | 324/209 X |

*Primary Examiner*—Gerard R. Strecker
*Assistant Examiner*—Warren S. Edmonds
*Attorney, Agent, or Firm*—Earl L. Larcher; Stephen D. Hamel; Michael F. Esposito

[57] ABSTRACT

The present invention is directed to a rapid nondestructive method for determining the extent of strain hardening in an article of tungsten-nickel-iron alloy. The method comprises saturating the article with a magnetic field from a permanent magnet, measuring the magnetic flux emanating from the article, comparing the measurements of the magnetic flux emanating from the article with measured magnetic fluxes from similarly shaped standards of the alloy with known amounts of strain hardening to determine the hardness.

2 Claims, 3 Drawing Figures

METHOD FOR DETERMINING THE HARDNESS OF STRAIN HARDENING ARTICLES OF TUNGSTEN-NICKEL-IRON ALLOY

The present invention was made as a result of a contract with the U.S. Department of Energy.

BACKGROUND OF THE INVENTION

The present invention relates generally to a method of determining the hardness of high density tungsten-nickel-iron alloys, and more particularly, to the measurement of the cross-sectional hardness of elongated articles formed of such alloys.

Armor-penetrating projectiles (penetrators) are military projectiles fabricated of materials having sufficient hardness for providing high level penetration of armor plating. The measure of effectiveness for a penetrator is the thickness of various armor plating which may be penetrated by the projectile at a particular velocity. The greater the penetrating ability of a penetrator the greater its effective range and the lower of required velocity the projectile.

It is generally accepted that an effective armor penetrating projectile must have sufficient strained strength, density and hardness and yet be of sufficient ductility to prevent the projectile from fragmenting prior to completion of the penetration. Also due to the exigencies of warfare, it is important that penetrators be highly reproducible and of reproducible effectiveness which necessitates that the material used for the fabrication of the penetrators be readily formed into penetrators having virtually uniform strength, hardness and ductility throughout. A satisfactory material for fabricating penetrators is a tungsten-nickel-iron alloy fabricated into penetrator form by practicing the method disclosed in assignee's U.S. Pat. No. 3,979,234, which issued Sept. 7, 1976, and is entitled "Process for Fabricating Articles of Tungsten-Nickel-Iron Alloy."

Generally, tungsten-nickel-iron alloys fabricated into penetrators by practicing the method of the aforementioned patent is achieved by forming a powder admixture of 85-95 wt. % tungsten with nickel and iron in a weight ratio of 5:5-8:2. Pressing the admixture into a compact, sintering the compact into a reducing atmosphere at a temperature in the range of 1200°-1420° C. to provide an article having at least 95% of the theoretical density; further heating the article to a temperature in the range of about 0.1°-20° C. above the liquidus temperature for a period of time sufficient to cause the formation of a liquid phase yet insufficient to induce slumping in the article; vacuum annealing the article by maintaining the article in vacuum at a temperature in the range of 700°-1420° C. for sufficient time to remove entrapped gases; and thereafter sufficiently cold working the article to provide the desired hardness therein.

The tungsten-nickel-iron alloy penetrators are strain hardened to sufficiently harden and strengthen the alloy for use in penetrator applications. This hardening is achieved by cold working in any desired manner such as by swaging. It has been found that the vacuum-annealed article may be cold worked to a hardness of 40 on the Rockwell C(Rc) scale and yet exhibit elongation of about 14%. The hardness is highly uniform throughout the cross section of these alloy articles since a variation of only about ±1 Rockwell C unit is normally present through any cross-sectional portion of the article over the length thereof. This high degree of uniform hardness is necessary for assuring the success of the penetrators in piercing armor plating. After cold working, the article may be readily machined to the desired penetrator dimensions.

Inasmuch as the method of fabricating armor penetrators described in the aforementioned patent is the process for forming the penetrators in which the hardness is to be measured by the present invention, the aforementioned patent is incorporated herein by reference.

Inasmuch as penetrators formed of the tungsten-nickel-iron alloys require strain hardening for providing satisfactory armor piercing capability, a rapid, nondestructive method is needed during the production of large quantities of penetrators for detecting and measuring the level of hardness in the penetrators.

SUMMARY OF THE INVENTION

Accordingly, it is the primary aim or objective of the present invention to provide a non-destructive method for accurately detecting and measuring the amount of hardness in elongated, strain-hardened articles of tungsten-nickel-iron alloys formed or fabricated in article form as described in assignee's aforementioned patent. Generally, the method of the present invention determines the amount of hardness through the cross-sectional portions over the length of an elongated article formed of a tungsten-nickel-iron alloy as described in assignee's aforementioned patent. This method comprises the steps of placing the article in a magnetic field of a permanent magnet to saturate a cross-sectional portion of the article with magnetic flux, measuring the magnetic flux emanating from the article, and then comparing this measurement of magnetic flux with measurements of magnetic fluxes taken from a standard of the same alloy and formed in a similar shape with a known amount of hardness in any given cross section to determine the amount of strain hardening over the length of the article. This method is highly accurate and can be readily automated for use in high-volume production of penetrators.

Other and further objects of the invention will be obvious upon an understanding of the illustrative method about to be described or will be indicated in the appended claims, and various advantages not referred to herein will occur to one skilled in the art upon employment of the invention in practice.

DETAILED DESCRIPTION OF THE INVENTION

The present invention is directed to a method for measuring crosssectional strained hardening along the length of an elongated article formed of a tungsten-nickel-iron alloy as described in the assignee's aforementioned patent. This method comprises the steps of passing the article through a magnetic field emanating from a permanent magnet and measuring the magnetic flux emanating from the article over the length thereof to determine extent of distortion of the magnetic field. The extent of distortion of the magnetic field is dependent upon the extent of strain hardening through the cross section of a longitudinal portion of the article disposed within the magnetic field. By comparing the measurements of the magnetic flux taken along the length of the article with measurements of magnetic flux from standards of the article of similar configurations and of known hardness, an accurate measurement of the crosssectional hardness of the article along the length thereof may be readily obtained.

Figure 1:
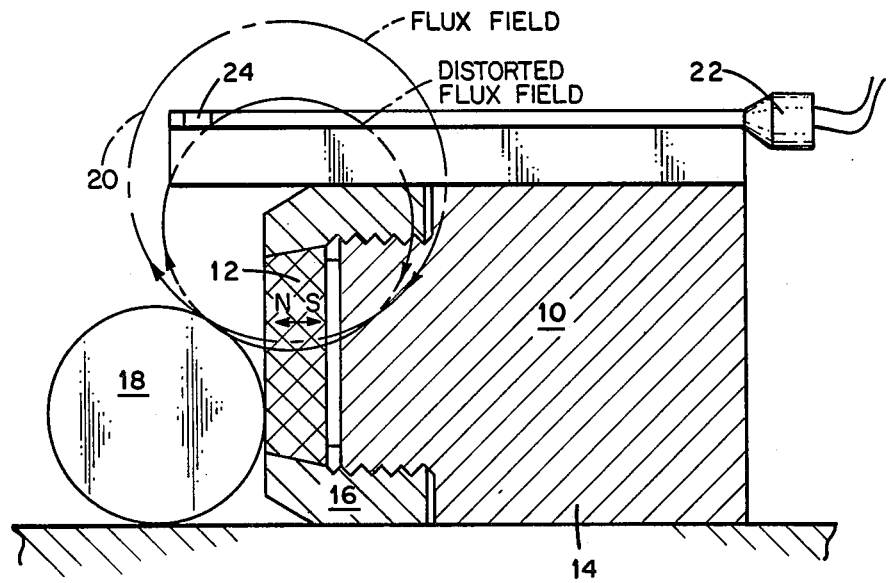
FIG. 1 is a schematic illustration showing a tungsten-nickel-iron alloy article disposed in the magnetic field of a permanent magnet for providing a level of magnetic flux emanation therefrom which is picked up by a suitable meter capable of measuring the level magnetic flux emanating from the article.

As shown in FIG. 1, a permanent magnet 12, formed of a suitable permanent magnetic material such as samarium-cobalt, is supported in an aluminum housing 14 through a non-magnetic coupling 16 of stainless steel or the like. As the article of tungsten-nickel-iron alloy, as generally shown in cylindrical format 18, is passed along a plane orthogonal to the drawing, the magnetic field 20 emanating from the magnet 12 is distorted by the article. This distortion in the magnetic flux is picked up by a suitable probe disposed in an advantageous position with respect to the magnetic field 20. For example, a Hall Gaussmeter 22 having a probe 24 disposed generally above the article 18 may be utilized for measuring the magnetic flux emanating from the tungsten-nickel-iron article as it is passed through the magnetic field 20 emanating from magnet 12. The magnet system and article 18 test bar may be suitably supported on a base 26 formed of a non-magnetic material such as stainless steel or the like.

In a test of the present invention, two elongate rods formed of 90 wt. % tungsten, 7 wt. % nickel and 3 wt. % iron alloy were formed with a length of 13.625 inches. These rods were uniformly tapered 30% over the length thereof by machining. These tapered rods were then mechanically swaged to a uniform diameter of 1.125 inches and a total length of 17.5 inches to provide a linearly graded reduction in the crosssectional area ranging from 0 to 30% over the length of the rods.

Figure 2:
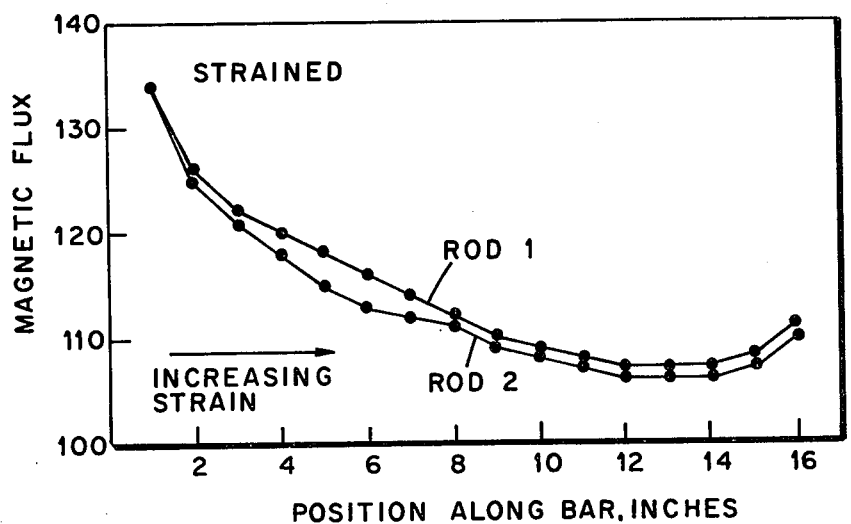
FIGS. 2 and 3 are graphs respectively showing the difference in magnetic flux and hardness as increasing strain occurs and the hardness along the length of two test rods of the tungsten-nickel-iron alloy swaged with increasing degrees of reduction over the length thereof. An embodiment of a flux measuring system has been chosen for the purpose of illustration and description of the method of the present invention. The embodiment illustrated is not intended to be exhaustive or to limit the practice of the subject method to the precise form of measurement system disclosed. It is chosen and described in order to best explain the principles of the invention and their application in practical use to thereby enable others skilled in the art to best utilize the invention in various modifications as are best adapted to the particular use contemplated.

These rods were then passed sequentially through the magnetic field 20 emanating from the magnet 12. As shown in FIG. 2, the static magnetic field 20 of the permanent magnet is considerably distorted by the presence of rods as a function of permeability in the rods. In other words, as the hardness of the rod increases the permeability of the rod deceases which results in an increase in the distortion of the magnetic field. As shown in the graph of FIG. 2, the magnetic flux undergoes a reduction as the diameter of rods 1 and 2 decreases as a result of increased cold working. Note that the extent of the magnetic flux emanating from each of the rods over the length thereof is substantially similar so as to provide an example of the accuracy of the subject method.

Figure 3:
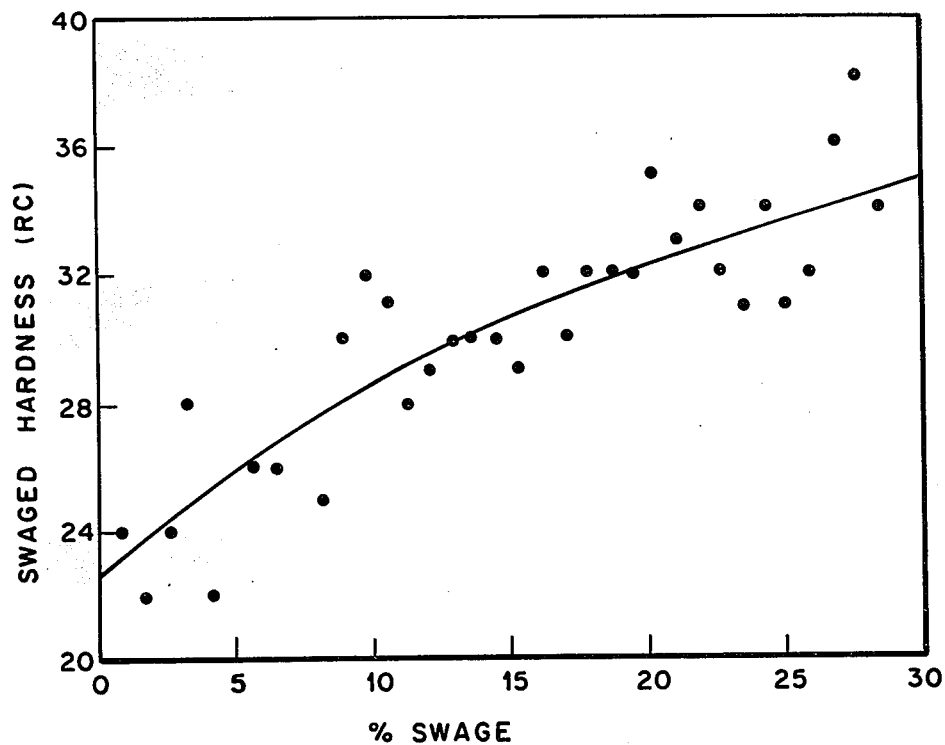

As shown in FIG. 3, the hardness of the rods increase linearly in Rockwell (Rc) units as the percent swage is increased from 0 to 30% over the length thereof. This linear relationship in swaging with respect to hardness provides an accurate gauge for forming the standards utilized in the present invention.

It will be seen that the present invention provides a method for accurately measuring the hardness in cold worked tungsten-nickel-iron alloys in a highly efficient and reproducible manner.

What is claimed is:

1. A method for measuring the extent of cross-sectional strain hardening along the length of an elongated cold-worked article formed of tungsten-nickel-iron alloy, consisting of the steps of passing the article through a magnetic field emanating from a permanent magnet to saturate a cross-sectional portion of the article with magnetic flux, measuring the magnetic flux emanating from the article to determine the extent of the distortion in the magnetic field due to the presence of the cross-sectional portion of the article therein with the extent of distortion being indicative of and increasing with the degree of strain hardening through the cross-sectional portion of the article within the magnetic field, and comparing the measurements of magnetic flux taken along the length of the article with measurements of magnetic flux taken from a standard of the alloy of known cross-sectional hardness and of a similar configuration to provide measurements of cross-sectional hardness through cross sections of the article along the length thereof.

2. The method claimed in claim 1, wherein the article comprises 85 to 95 wt. % tungsten and the remainder nickel and iron in a nickel-iron ratio of 5:5 to 8:2.

* * * * *